US005487752A

United States Patent [19]
Salo et al.

[11] Patent Number: 5,487,752
[45] Date of Patent: Jan. 30, 1996

[54] AUTOMATED PROGRAMMABLE STIMULATING DEVICE TO OPTIMIZE PACING PARAMETERS AND METHOD

[75] Inventors: Rodney W. Salo, Fridley; Julio C. Spinelli, Shoreview; Bruce A. Tockman, Minneapolis, all of Minn.

[73] Assignee: Cardiac Pacemakers, Inc., St. Paul, Minn.

[21] Appl. No.: 339,567

[22] Filed: Nov. 15, 1994

[51] Int. Cl.$^6$ ............................................. A61N 1/365
[52] U.S. Cl. ............................. 607/17; 607/23; 607/22
[58] Field of Search ................................. 607/18, 21, 22, 607/23, 24, 27, 17

[56] References Cited

U.S. PATENT DOCUMENTS 4,303,075  12/1981  Heilman et al. .
5,024,222  6/1991  Thacker .

OTHER PUBLICATIONS

H. Kataoka, "Hemodynamic Effect of Physiological Dual–Chamber Pacing in a Patient with End–Stage Dilated Cardiomyopathy: A Case Report", PACE 14:1330–1335 (Sep. 1991).

Primary Examiner—William E. Kamm
Assistant Examiner—Scott M. Getzow
Attorney, Agent, or Firm—Haugen and Nikolai

[57] ABSTRACT

A method and apparatus for automatically optimizing a cardiac performance parameter of the heart, such as its cardiac output mean arterial pressure $pO_2$ or $pCO_2$. The performance parameter is optimized by periodically pacing the heart for a short period of time with stimulating pulses having a modified pacing parameter value. The intrinsic operation of the heart is monitored a majority of the time and establishes a baseline value for the cardiac performance parameter. The heart is then paced with the modified pacing parameter value during an interval that is approximately a 1:4 ratio with respect to the baseline monitoring interval. The method of the present invention can be achieved using a totally implanted pacemaker, an implanted pulse generator in combination with external equipment communicating with the pacemaker via telemetry, or by using equipment located external the patient.

18 Claims, 3 Drawing Sheets

5,487,752

AUTOMATED PROGRAMMABLE STIMULATING DEVICE TO OPTIMIZE PACING PARAMETERS AND METHOD

BACKGROUND OF THE INVENTION

1. Field of the Invention

This invention relates generally to cardiac stimulating apparatus, and more particularly to a method and device for optimizing the cardiac pacing parameters of such apparatus. This invention finds particular use with cardiac stimulators for use by patients suffering from chronic congestive heart failure (CHF) and having an unacceptably low cardiac output.

2. Discussion of the Prior Art

Patients suffering from CHF typically manifest a degraded cardiac function, such as an abnormally low cardiac output. While adaptive rate pacing may be utilized to increase cardiac output by increasing heart rate with increased metabolic demand, such an increased heart rate necessitates that the heart work harder to pump a sufficient quantity of blood to meet the needs of the body. Patients suffering from CHF may not have sufficient reserve to accommodate the higher rate.

Prior art manual and automated techniques are known whereby one or more of the pacing cycle parameters of a cardiac stimulator, such as R—R interval, A–V delay, and pacing mode can be adjusted to help optimize cardiac output and cardiac pressure parameters for a given pacing rate.

One standard current approach is to use a pacing system analyzer under manual control while monitoring one or more physiological variables. The pacing system parameters are manually varied and the optimum value is assumed to be that at which the maximum (or occasionally, minimum) value of the physiological variable occurred. There are several disadvantages to this approach. First, this manual method is overly time-consuming. Secondly, data gathering is not automated, thus resulting in possible errors during the data transcription. Thirdly, during the time of the procedure, the underlying physiologic substrate may change resulting in inaccurate assessment of cardiac performance. The effect is exacerbated by the length of the procedure.

One such automated technique is disclosed in U.S. Pat. No. 5,024,222 to Thacker. The pertinent aspect of this patent involves scanning through a series of available A–V pulse delays at a fixed heart rate, while monitoring a measure of cardiac output, and then setting the A–V pulse delay to the value which resulted in the maximum cardiac output. The drawback with this automated technique for pacing parameter optimization is that the body's natural reflexes have time to respond to each pacing parameter setting, potentially masking differences between settings. In addition, this technique does not include monitoring of the underlying substrate by returning often to a baseline or intrinsic heart conditions.

U.S. Pat. No. 4,303,075 to Heilman, et al. discloses a method and apparatus for maximizing stroke volume through atrio-ventricular pacing using implanted cardioverter/pacer. This patent discloses optimizing the A–V pulse delay by maximizing the measured value of a parameter, e.g., stroke volume measured by electrical impedance. For additional background on the impact of implementing different A–V pulse delays on cardiac function in a patient with congestive heart failure (CHF), reference is made to an article authored by H. Kataoka, entitled "Hemodynamic Effect of Physiological Dual-Chamber Pacing in a Patient with End Stage Dilated Cardiomyopathy": "A Case Report", PACE, 14:1330–1335 (09/1991).

The optimization of pacing parameters is not as critical in patients with relatively normal, healthy hearts. These patients have the necessary cardiac reserve to compensate for programming errors. It is patients with depressed cardiac function that are much more sensitive to factors such as pacing rate and A–V delay. Current optimization techniques, if they are used at all, are time-consuming and prone to error.

The present invention permits the rapid and accurate automated determination of optimum pacemaker (or AICD) settings. These settings can be either automatically determined and established by the pacemaker device, or determined by an external programmer/monitor and later programmed into the pacemaker device, which is already implanted or subsequently implanted by a physician.

OBJECTS

It is accordingly a principal object of the present invention to provide a method and apparatus whereby performance parameters of a cardiac rhythm management device can be automatically, and quickly, established at an optimum setting.

It is a further object of the present invention to provide a method and apparatus whereby the performance parameter of a cardiac stimulater can be quickly determined without the effects of such parameters being subject to, and masked by, the body's physiologic reflexes to the change.

Still yet another object of the present invention is to provide a method and apparatus whereby the optimum cardiac performance parameter of a cardiac pacemaker or AICD device can be rapidly determined and programmed into that device, either using an external programmer, or achieved automatically in the implanted device incorporating the capability of performing this function.

Another object of the present invention is to provide a method and apparatus whereby the cardiac performance parameters are optimized, without the need to adjust or increase an intrinsic pulse rate of the patient.

DESCRIPTION OF THE PREFERRED EMBODIMENT

Figure 1:
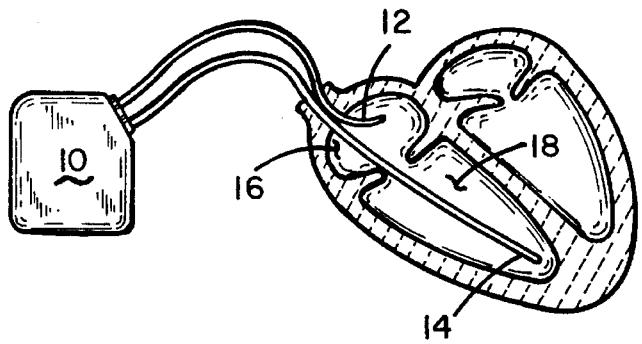
FIG. 1 is a simplified representation of the heart showing the manner in which a pacemaker is connected thereto through insertion of suitable unipolar or multi-polar leads into both the right atrium, right ventricle and optionally into the left ventricle.

Referring now to FIG. 1, a simplified diagram of one way that an implanted pacemaker 10 may be adapted to a patient's heart is shown. Three bipolar or unipolar leads 12 and 14 are shown being positioned in a separate chamber of the heart, the first lead 12 being positioned in the right atrium, and the second lead 14 being positioned in the right ventricle 18. For bi-ventricular pacing, a third lead would be coupled to the left ventricle. The distal tip electrode of each lead is positioned within or on a respective chamber as is well known in the art, to effectively achieve bipolar or unipolar pacing and sensing. The time delay between when the atrium contracts and when the ventricle contracts is commonly known as the A–V interval. The intrinsic A–V interval is defined as when the heart is beating unassisted. This A–V intrinsic delay generally shorter than the A–V delay set into a cardiac stimulator so that the intrinsic A–V interval will have priority.

Figure 2:
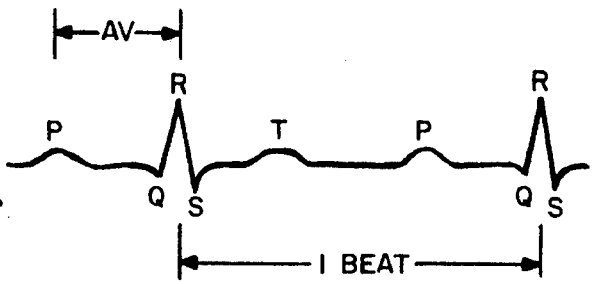
FIG. 2 is an ECG timing diagram illustrating the normal, non-paced operation of the heart as sensed through conventional skin ECG electrodes.

Referring now to FIG. 2, an ECG timing diagram illustrating the hemodynamics of the normal heart is shown. The time delay between the P-wave and the R-wave corresponds to the intrinsic A–V interval as previously described, this period normally being in the range of 150 to 250 milliseconds. The ECG timing diagram shown is representative of a normal, un-paced, beating heart. As will be described shortly, the time period between the P-wave and a paced R-wave must necessarily be shorter than the intrinsic A–V delay of the cardiac stimulator whose parameter is to be optimized.

Figure 3:
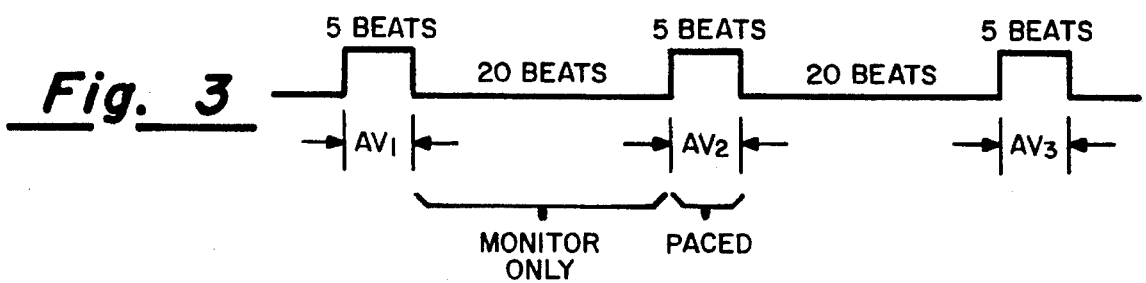
FIG. 3 is a timing diagram according to the present invention illustrating the intervals at which the heart is periodically paced with a selected pacing cycle parameter, such as a reduced A–V pulse delay, followed by a relatively long monitoring or non-paced interval representing a baseline between the paced intervals.
Figure 4:
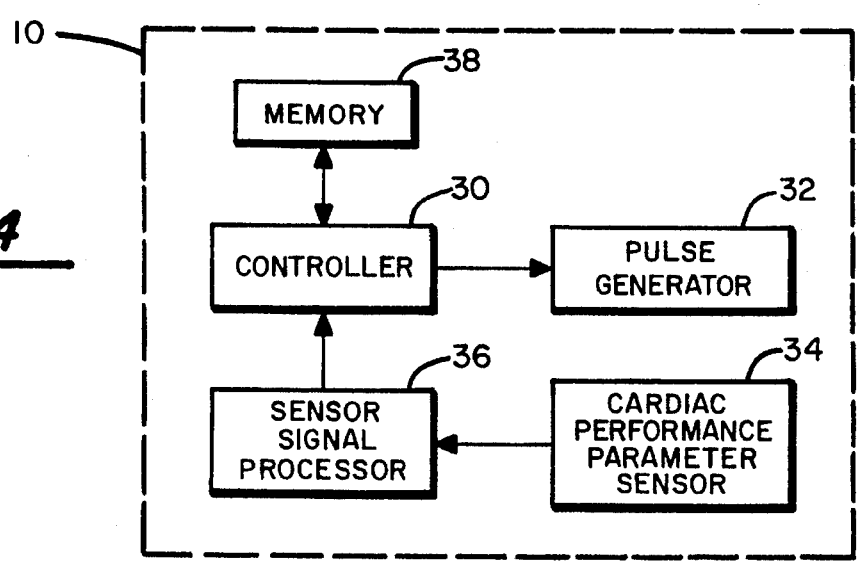
FIG. 4 is a simplified block diagram of a pacemaker according to the present invention including a sensor signal processor capable of optimizing physiologic parameters of the heart, such as cardiac output.

Referring now to FIGS. 3 and 4, the method according to the present invention of assessing and optimizing an intrinsic cardiac performance parameter of the heart is shown. As is graphically illustrated, pacemaker 10 includes means for monitoring and pacing at least two chambers of the heart with pulses providing predetermined A–V intervals. The paced A–V interval is changed for a relatively few beats, e.g., 5 beats and then is allowed to return to a baseline value for a relatively long time, e.g., 20 beats.

According to the present invention, the cardiovascular system is in a baseline steady-state a majority of the time, and is only perturbed from this state for very short intervals, shown at $AV_1$, $AV_2$, $AV_3$, etc. The interval duration of these perturbations is selected to be shorter than the time period necessary for physiological reflexes to respond to the perturbations. According to the present invention, a cardiac performance parameter of the heart, such as cardiac output, is assessed during both the baseline interval (normal sinus or intrinsic rhythm) and the paced intervals. It is then determined whether the cardiac performance parameter improved, remained the same, or degraded from the baseline value. These chosen intervals of 20 beats baseline and 5 beats with a changed pacing parameter represent a 4:1 ratio between monitoring and controlling the cardiac pacing cycle parameter.

The method according to the present invention is particularly efficacious in optimizing a stimulator's pacing parameters for CHF patients since the body's reflexes do not have time to respond to each modified pacing cycle parameter during the short pulsed intervals. The A–V interval can be changed and the effects of the change noted during the short pacing sequence, and then the heart is allowed to beat normally, without the body adapting to this controlled procedure. Thus, the hemodynamic effects of the modified A–V interval are not masked.

While the A–V delay interval may be the preferred cardiac cycle parameter monitored and controlled in establishing the optimum cardiac performance parameter, it will be recognized by those skilled in the art that other pacing cycle parameters such as pacing pulse width, pulse amplitude, pulse rate, $A_R$–$A_L$ delay, $V_R$–$V_L$ delay, etc. can be periodically dithered during the paced and non-paced intervals and the resulting effect on cardiac performance noted. Moreover, while cardiac output is the intended cardiac performance parameter to be optimized, it is also to be recognized by those skilled in the art that other cardiac performance parameters can be optimized as well. In addition to optimizing a cardiac performance parameter, such as cardiac output, by periodically dithering some pacing cycle parameter, it is also contemplated that the pacing mode can be periodically changed and the effect on the cardiac performance parameter noted. Hence, the pacing mode might be changed from right ventricular pacing to left ventricular pacing or to bi-ventricular pacing or to bi-ventricular pacing with offset. AV hysteresis may also be a dithered parameter, AV hysteresis being the difference between the AV optimum for atrial pacing and the AV optimum for atrial sensing.

Referring now to FIG. 4, the pacemaker 10 capable of performing the method according to the preferred embodiment of the present invention is shown. The pacemaker 10 is seen to include a microprocessor based controller 30 controlling a conventional pulse generator 32 for stimulating one or both atrial chambers and one or both ventricular chambers. A cardiac output sensor 34 is adapted to be positioned within the heart. It is known that impedance plethysmography techniques involving sensing electrodes in the right ventricle can be used to measure stroke volume and the stroke volume multiplied by heart rate yields cardiac output. Signal processor 36 performs this function. Controller 30 controls pulse generator 32 as a function of the information provided by the sensor signal processor 36, as will now be discussed.

Figure 5:
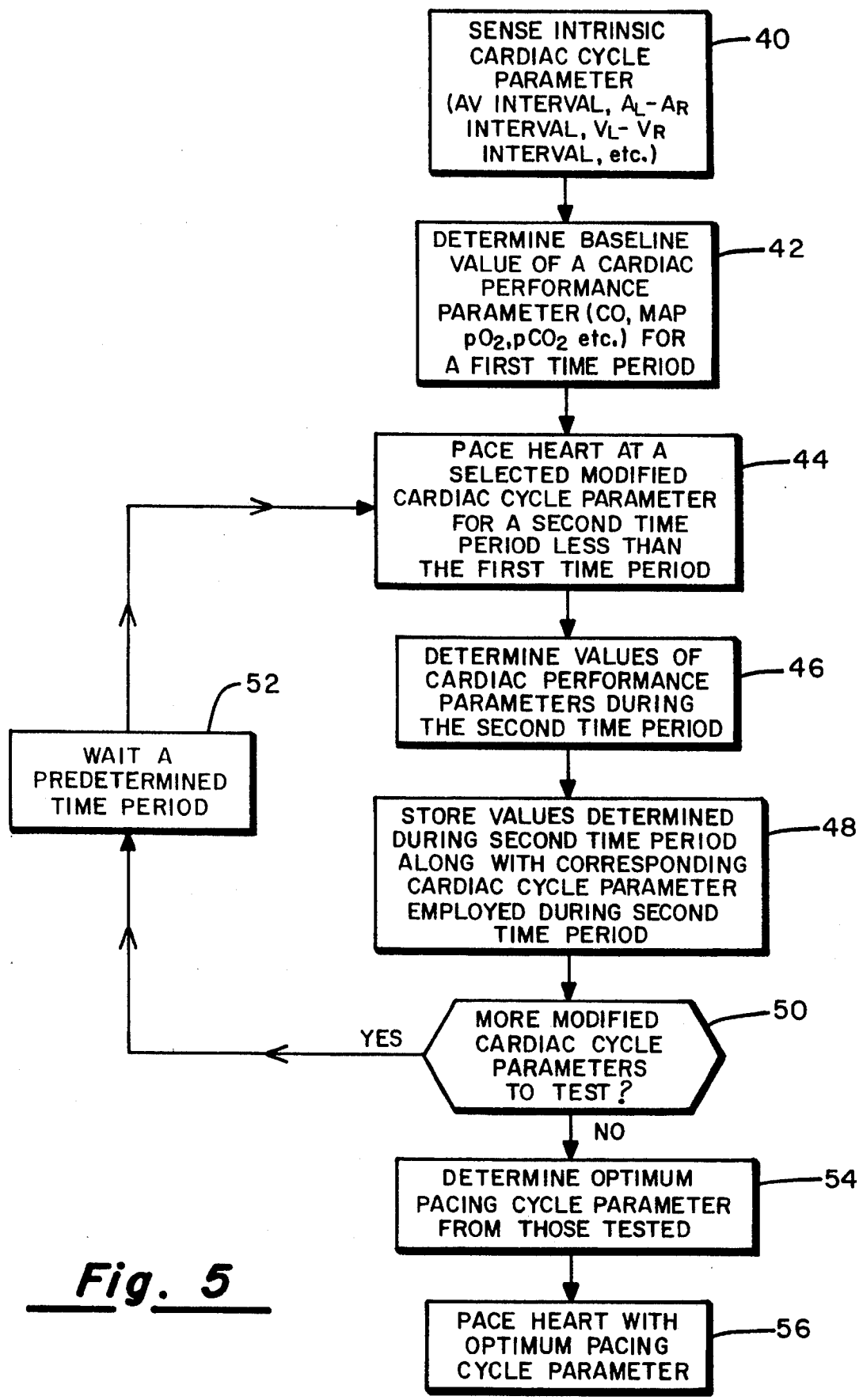
FIG. 5 is a flow diagram of the algorithm executed by the controller of FIG. 3 to determine and establish an optimum cardiac pacing cycle parameter.

Turning now to FIG. 5, the algorithm by which the present invention achieves optimizing a cardiac performance parameter is shown. By way of illustration, the present invention will be described as optimizing the cardiac output of the heart, although as mentioned above, other cardiac performance parameters, such as mean arterial pressure and even respiratory parameters including $pO_2$, $pCO_2$, etc., could be optimized according to the method of the present invention as well. Also, by way of illustration, the cardiac pacing cycle parameter to be adjusted to achieve optimization will be chosen to be the A–V delay for the RV pacing mode. Other cardiac pacing cycle parameters can be monitored and controlled as well. The discussion of the algorithm graphically illustrated in FIG. 5 is made with reference to FIG. 3, which will be referred to periodically. The cardiac stimulator, here represented by a bradycardia pacemaker is assumed to be implanted in the patient and positioned for dual chamber pacing.

At block 40, controller 30 ascertains the natural or intrinsic cardiac cycle parameter, e.g., A–V delay of the heart, for a first period of time, this period being the time for 20 beats to occur in the exemplary embodiment. Controller 30 ascertains this natural A–V delay from sensor signal processor 36.

At block 42, controller 30 ascertains the baseline value of a cardiac performance parameter, e.g., cardiac output, from the sensor signal processor 36. Sensor signal processor 36 calculates the cardiac output by determining intracardiac impedance between electrodes 14 and 16 and associated ring electrodes, as is well-known in the art. For those desiring more detailed information, reference is made to the Salo et al. U.S. Pat. No. 5,190,035. However, other means for determining cardiac output can be implemented as well according to well-known techniques, such as those determining aortic flow using Doppler shifting or by using perfusion sensors, or other invasive and non-invasive techniques known in the he art.

At step 44, controller 30 instructs pulse generator 32 to stimulate the heart, via electrodes 14 and 16, for, say, a comparatively short, second period of time, chosen to be the time for five beats to occur. This pacing interval is reflected as the short period labeled A–V in FIG. 3. During this short pacing interval, the ventricle or ventricles is/are paced at essentially the same pacing rate as the intrinsic pulse rate. However, during the short interval the heart is paced with a modified cardiac cycle parameter, e.g. A–V interval, $(A-V)_1$, which is shorter than the intrinsic A–V interval sensed and determined in step 40. While pacing the heart with this changed A–V interval represented by block 44, controller 30 ascertains the values of the resulting selected cardiac performance parameter (cardiac output) from signal processor 36 (block 46). The cardiac output is determined by signal processor 36 using the same technique as that chosen in step 42.

Block 48 indicates that at the end of this five-beat pacing window in which the A–V interval is altered to a value $(A-V)_1$, controller 30 stores in memory 38 the determined cardiac output associated with the delay interval $(A-V)_1$.

Next, at decision block 50, controller 30 determines if further short series of pacing cycles with modified A–V delays are to be tested and the resulting cardiac output measurements determined and stored. If there are more pacing cycles to be executed, the algorithm proceeds to block 52 where controller 30 waits a predetermined period of time, preferably 20 beats, as shown in FIG. 3, and then again paces the heart at the next selected modified pacing cycle parameter for a short period of time associated with five successive beats. In FIG. 3, this is represented as interval $(A-V)_2$. Thereafter, the steps represented by blocks 46 and 48 are performed again as previously described.

This loop iterates until all modified pacing cycle parameters (AV-delays) programmed into memory 38 to be tested are executed. Pacing with these modified A–V delays takes place during successive short pacing intervals represented as $(A-V)_3$ and so on. Again, as previously discussed, these short pacing intervals with modified A–V delay values, are separated from one another by a relatively long, programmable period of time. While a ratio of 20 beats unpaced to five beats paced has been found effective, limitation to this specific ratio is not to be inferred.

After controller 30 determines at block 50 that all modified A–V delay values programmed have now been tested, and the associated cardiac outputs calculated and stored in memory 38, the algorithm exits from the loop to block 54 where the optimum pacing cycle parameter (A–V delay interval) is determined as being that which yielded the greatest cardiac output. Next, at block 56 the stimulator's A–V interval is set to the value where the heart will be paced by pulse generator 32 at a selected pulse rate and with the ascertained optimum A–V delay.

Figure 6:
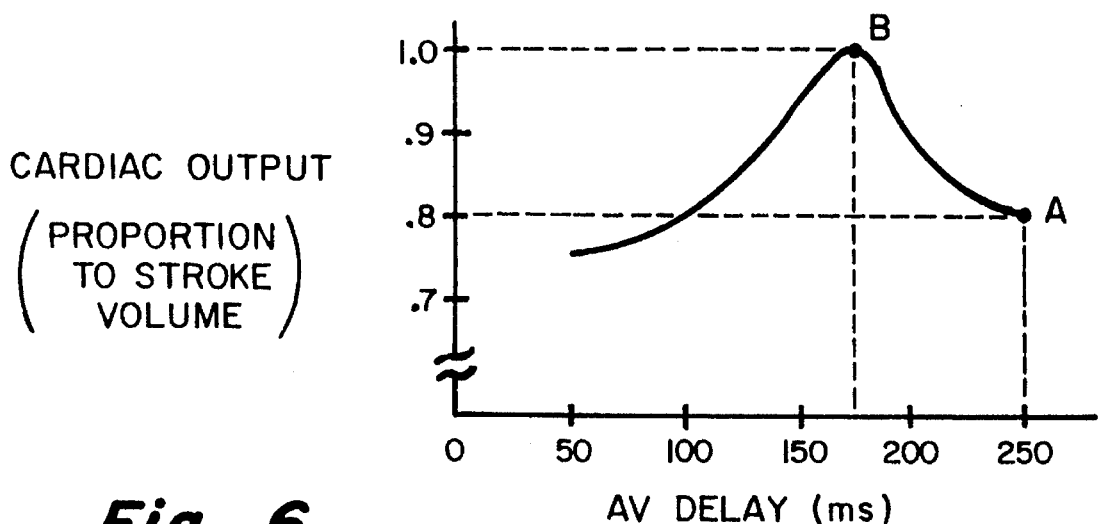
FIG. 6 is a graph of cardiac output as a function of the A–V pulse delay, illustrating the cardiac output being maximum at an A–V pulse delay of 175 milliseconds.

Referring now to FIG. 6, there is illustrated a plot of cardiac output as a function of pacer A–V delay. The intrinsic A–V delay, corresponding to 250 milliseconds, is shown at point A, and the optimum and maximum cardiac output is shown at point B, corresponding to an A–V delay of 175 milliseconds. In accordance with the methodology of the present invention, a plurality of A–V delays each different from the intrinsic A–V delay and from each other are used. The graph in FIG. 6 is provided only for illustrative purposes, and the A–V delay which yields the optimum cardiac output will typically be different for each patient.

One of the principal features of a cardiac stimulator comprising a preferred embodiment of the present invention is that cardiovascular performance is monitored for a baseline period of time, and then pacing is allowed to occur for relatively short periods of time with cardiac pacing cycle parameter that is different each successive time. By following this approach, the heart is alternately monitored and paced so that the effects of pacing the heart according to a pacing cycle being different from the intrinsic cycle can be ascertained, without being masked.

Figure 7:
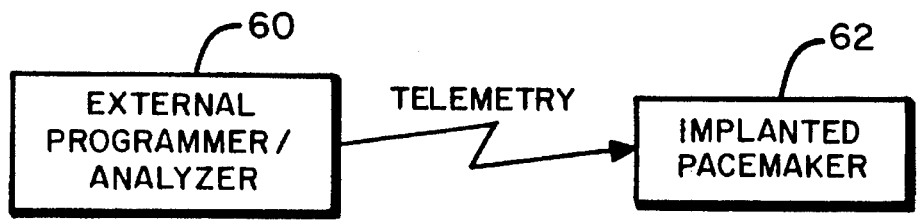
FIG. 7 is a block diagram of an alternative preferred embodiment of the present invention, whereby the control and analysis circuitry determining the optimum cardiac pacing cycle parameter is provided external to the patient, this parameter being programmed into the implanted pacemaker via telemetry.
Figure 8:
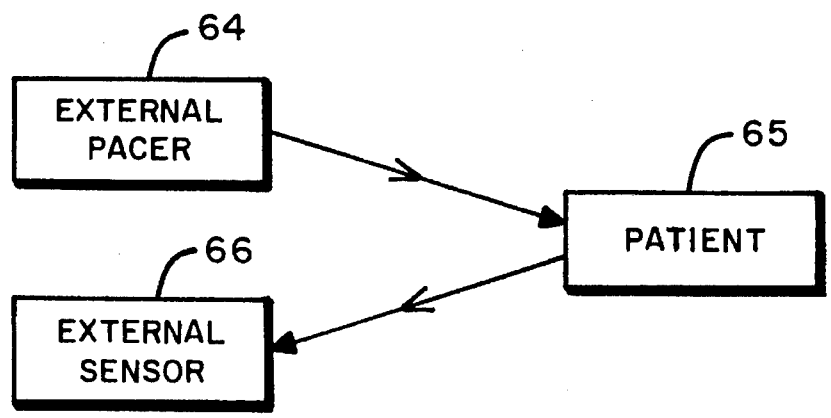
FIG. 8 is a block diagram of yet another alternative preferred embodiment of the invention whereby both the control and analysis circuitry as well as the sensors reside external the patient during the examination procedure.

The preferred embodiment described above was shown as incorporated into an implanted cardiac pacemaker. However, it is within the scope of the present invention that the foregoing methodology can be embodied in an external programmer/analyzer 60 controlling an implanted pacemaker 62 via telemetry, as shown in FIG. 7 or connected directly to the pacing leads. The software performing the method of the present invention is executed in the external programmer/analyzer 60, rather than being resident within pacemaker 10. Referring to FIG. 8, it is also within the scope of the present invention that the sensors associated with sensor signal processor 36 be positioned external the patient as well. Here, a cardiac performance parameter, such as cardiac output, is determined using non-invasive techniques, such as monitoring blood pressure. Thus, limitation to location of the sensors, or where the control circuitry is located, is not to be inferred.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A cardiac stimulator system comprising:
   (a) a cardiac stimulator for normally applying cardiac stimulating pulses having programmable pacing cycle parameters to a heart during a first predetermined time interval sufficiently long to establish a baseline condition for a cardiac performance parameter;
   (b) means for measuring and storing values of said cardiac performance parameter;
   (c) means for periodically changing one of said programmable pacing cycle parameters during a second predetermined time interval that is only a small fraction of said first predetermined time interval;

(d) means including said means for measuring and storing values of said cardiac performance parameter for measuring and storing values of said cardiac performance parameters during successive ones of said first and second predetermined time intervals; and (e) means for determining whether an improvement in said cardiac performance parameter over the baseline condition occurs during ones of said second predetermined time intervals.

2. The cardiac stimulator system as in claim 1 and further including:

(a) means for setting said programmable pacing parameter to a value corresponding to that determined to afford the maximum improvement in said cardiac performance parameter over the baseline condition.

3. The cardiac stimulator system as in claim 1, wherein said cardiac performance parameter is cardiac output.

4. The cardiac stimulator system as in claim 1 wherein said cardiac performance parameter is mean arterial pressure.

5. The cardiac stimulator system as in claim 1 wherein said cardiac performance parameter is one of $pCO_2$ and $pO_2$.

6. The cardiac stimulator system as in claim 1, wherein said programmable pacing parameter is an A–V interval between the occurrence of a paced or intrinsic P-wave and the application of one of said cardiac stimulating pulses to the heart.

7. The cardiac stimulator system as in claim 1 wherein said programmable pacing parameter is any one of pacing pulse width, pacing pulse rate, pacing pulse amplitude, atrial pacing interval and ventricular pacing interval.

8. The cardiac stimulator system as in claim 1, wherein said device is adapted to be totally implanted within a patient.

9. The cardiac stimulator system as in claim 1, wherein said cardiac stimulator is totally implantable and said means for measuring and storing and said determining means are external to the patient.

10. The cardiac stimulator system as in claim 9 and further including telemetry means in said cardiac stimulator and said means for measuring and storing for permitting two-way communication there between.

11. The cardiac stimulator system as in claim 1, wherein said cardiac stimulator, said means for measuring and storing, said means for periodically changing one of said programmable pacing cycle parameters, and said determining means are external to a patient.

12. A method of optimizing a cardiac performance parameter of a heart, comprising the steps of:

monitoring an intrinsic baseline cardiac pacing cycle parameter of a cardiac stimulator device for a first time period;

modifying said cardiac pacing cycle parameter by applying stimulating pulses to the heart for a second time period, said second time period being substantially shorter than said first time period;

comparing a cardiac performance parameter of the heart during both said first time period and said second time period, and generating an output indicative of said comparison; and adjusting said baseline cardiac pacing cycle parameter as a function of said output.

13. The method as specified in claim 12 wherein the step of modifying said cardiac pacing cycle parameter comprises modifying an A–V interval of said cardiac stimulator device during said second time period.

14. The method as specified in claim 12 wherein the step of modifying said cardiac pacing cycle parameter comprises modifying any one of pacing pulse width, pacing pulse-rate, pacing pulse amplitude, atrial pacing interval and ventricular pacing interval.

15. The method as specified in claim 12 wherein said cardiac performance parameter comprises cardiac output of the heart, and further including the step of adjusting an A–V interval of the cardiac stimulator device as a function of compared cardiac output values.

16. The method as in claim 12 wherein said cardiac performance parameter comprises any one of $pCO_2$ and $pO_2$, and further including the step of adjusting any one of the cardiac stimulator device's pacing pulse rate, pacing pulse width, pacing pulse amplitude, atrial pacing interval and ventricular pacing interval as a function of compared $pCO_2$ and $pO_2$ values.

17. The method as specified in claim 12 and further comprising the step of using a cardiac stimulator device implanted in the patient to automatically perform the steps recited, and pacing said heart with the adjusted baseline cardiac pacing cycle parameter if a corresponding cardiac performance parameter improves.

18. The method as specified in claim 12 further comprising the step of providing an external programmer to manually control the implanted cardiac stimulator device.

* * * * *